(12) United States Patent
Hutchenson et al.

(10) Patent No.: US 7,999,057 B2
(45) Date of Patent: *Aug. 16, 2011

(54) GAS-PHASE PROCESS FOR THE SYNTHESIS OF DIAMINOPYRIDINES FROM GLUTARONITRILES

(75) Inventors: Keith W. Hutchenson, Lincoln University, PA (US); Aaron Minter, Wilmington, DE (US); Gregg Sunshine, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/169,152

(22) Filed: Jul. 8, 2008

(65) Prior Publication Data

US 2010/0010189 A1  Jan. 14, 2010

(51) Int. Cl.
*C08G 63/00* (2006.01)
*C08G 63/02* (2006.01)

(52) U.S. Cl. ........ 528/208; 528/176; 528/190; 528/198; 544/82

(58) Field of Classification Search .................... 544/82; 546/250; 528/176, 190, 198, 208
See application file for complete search history.

(56) References Cited

U.S. PATENT DOCUMENTS

| | | | |
|---|---|---|---|
| 2,816,879 A | 12/1957 | Wittenbecker | |
| 3,554,966 A | 1/1971 | Jones et al. | |
| 4,051,140 A | 9/1977 | Gelbein et al. | |
| 4,086,237 A | 4/1978 | Daum | |
| 4,110,412 A | 8/1978 | Danzig et al. | |
| 4,153,783 A | 5/1979 | Gagliani et al. | |
| 4,386,209 A * | 5/1983 | McGill et al. | 546/311 |
| 4,451,642 A | 5/1984 | Frazer et al. | |
| 4,603,207 A | 7/1986 | DiCosimo et al. | |
| 4,736,015 A | 4/1988 | Rabilloud et al. | |
| 4,737,571 A | 4/1988 | Hodge et al. | |
| 4,876,348 A | 10/1989 | DiCosimo et al. | |
| 5,028,713 A | 7/1991 | DiCosimo et al. | |
| 5,061,784 A | 10/1991 | Mueller et al. | |
| 5,066,809 A | 11/1991 | Suresh et al. | |
| 5,674,969 A | 10/1997 | Sikkema et al. | |
| 5,693,227 A | 12/1997 | Costa | |
| 5,939,553 A * | 8/1999 | Reichwein et al. | 546/250 |
| 5,959,553 A * | 9/1999 | Raswant | 340/907 |
| 6,118,003 A | 9/2000 | McAteer et al. | |
| 6,228,285 B1 * | 5/2001 | Wang et al. | 252/299.01 |
| 7,683,157 B2 | 3/2010 | Allen | |
| 2003/0083428 A1 * | 5/2003 | Bauriedel et al. | 524/589 |
| 2006/0287475 A1 | 12/2006 | Allen et al. | |
| 2010/0029948 A1 * | 2/2010 | Minter et al. | 546/250 |
| 2010/0056749 A1 * | 3/2010 | Minter et al. | 528/220 |

FOREIGN PATENT DOCUMENTS

| | | |
|---|---|---|
| BR | 2 165 844 | 4/1986 |
| CA | 2 355 316 | 6/2005 |
| WO | 94/25506 A1 | 11/1994 |

OTHER PUBLICATIONS

Chemistry of Heterocyclic Compounds, vol. 32, No. 2, 1996. Synthesis of Pyridine Bases by The Chichibabin Method, R. S. Sagitullin et al. (Review).*
Cotton et al., Advanced Inorganic Chemistry, 2nd Edition, 1966, Interscience, John Wiley & Sons.
Fogler, Elements of Chemical Reaction Engineering, 2nd Edition, 1992, pp. 10-19 & pp. 106-142.
Kumar et al., Chelating Copolymers Containing Photosensitive Functionalities, Macromolecules, 1984, vol. 17:2463-2467.
Millich et al., The Interfacial Preparation of Polyureas, Interfacial Synthesis, 1977, vol. 2, pp. 277-288.

* cited by examiner

*Primary Examiner* — Terressa M Boykin

(57) ABSTRACT

A gas-phase, continuous process is provided for the manufacture of 2,6-diaminopyridine and related compounds from glutaronitriles, which are used industrially as compounds and as components in the synthesis of a variety of useful materials. The synthesis proceeds by means of a dehydrogenative aromatization process.

20 Claims, 1 Drawing Sheet

GAS-PHASE PROCESS FOR THE SYNTHESIS OF DIAMINOPYRIDINES FROM GLUTARONITRILES

TECHNICAL FIELD

This invention relates to the manufacture of diaminopyridines and related compounds, and to the industrial use thereof for the synthesis of other useful materials.

BACKGROUND

The compound 2,6-diaminopyridine ("DAP"), which is represented by the structural formula shown below:

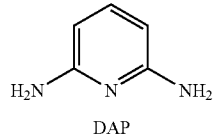

DAP is a useful starting material for preparing monomers for rigid rod polymers such as those described in WO 94/25506, as well as for the preparation of dyes, metal ligands, medicines and pesticides.

It is known to prepare DAP by means of the Chichibabin amination reaction, in which pyridine is reacted with sodium amide in an organic solvent. This is a complicated reaction, however, requiring relatively severe conditions (e.g. 200° C. at elevated pressure). Additionally, handling the sodium amide and isolating the desired product from this complex mixture are difficult operations to perform on a commercial scale.

The synthesis of 2,6-diaminopyridine and related compounds from glutaronitriles or glutarimidines may be described as proceeding via a dehydrogenative aromatization reaction. A process for the preparation of 2,6-diaminopyridine and related compounds from glutaronitriles and related compounds by contacting an acyclic dinitrile compound with a chemical oxidant and/or a dehydrogenation catalyst in liquid ammonia neat or in a mixture of ammonia and a polar, aprotic solvent, and heating the reaction mixture in a closed vessel, is described in U.S. Provisional Application No. 60/876,577 (filed 21 Dec. 2006), which is by this reference incorporated in its entirety as a part hereof for all purpose. A process for the preparation of 2,6-diaminopyridine and related compounds from glutarimidines and related compounds by contacting a glutarimidine with a chemical oxidant and/or a dehydrogenation catalyst in liquid ammonia neat or in a mixture of ammonia and a polar, aprotic solvent, and heating the reaction mixture in a closed vessel, is described in U.S. Provisional Application No. 60/876,557 (filed 21 Dec. 2006), which is by this reference incorporated in its entirety as a part hereof for all purpose.

British Patent 2,165,844 discloses the gas-phase conversion of glutaronitrile to pyridine in the presence of hydrogen over a palladium on silica catalyst. U.S. Pat. No. 4,876,348 discloses a gas-phase process for making 3-cyanopyridine by dehydrocyclization of 2-methylglutaronitrile over supported catalysts to make a mixture of 3-methylpyridine and 3-methylpiperidine, and reacting such mixture with ammonia over various oxide catalysts. U.S. Pat. No. 5,066,809 discloses a gas-phase process for making 3-methylpyridine by contacting 2-methylglutaronitrile in admixture with hydrogen gas with a supported catalyst.

Despite these existing processes to make pyridines, a need remains for a process for the gas-phase preparation of aminopyridines, and in particular DAP and related compounds.

SUMMARY

The inventions disclosed herein include processes for the preparation of diaminopyridines and related compounds, processes for the preparation of products into which diaminopyridines and related compounds can be converted, and the products obtained and obtainable by such processes.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

In one embodiment hereof, this invention provides a process for the synthesis of a compound as represented by the following structure of Formula (I)

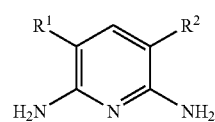

by (a) providing a compound as represented by the following structure of Formula (II)

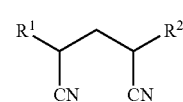

in the form of a gas, (b) providing ammonia gas, or a mixture of ammonia gas and a carrier gas, (c) heating a heterogeneous dehydrogenation catalyst, and (d) contacting the Formula II compound and the ammonia, or mixture with carrier gas, in the presence of the catalyst to produce a Formula (I) product; wherein $R^1$ and $R^2$ are each independently selected from H and a hydrocarbyl group.

In another embodiment hereof, this invention provides a process for preparing a Formula (I) compound, as described above, that further includes a step of subjecting the Formula (I) compound to a reaction (including a multi-step reaction) to prepare therefrom a compound (such as that useful as a monomer), oligomer or polymer.

An advantageous feature of the processes hereof is that, since they are conducted in the gas phase, they may also be conducted in a continuous manner thereby resulting in a significant decrease in overall reaction time and pressure, and enabling component recycle without isolation. For example, particularly when the process hereof is continuous, it may be carried out under mild reaction conditions [e.g. pressures less than about 100 psi (0.7 MPa)] at short reaction times. Such features combine to produce an economically favorable process.

BRIEF DESCRIPTION OF THE DRAWINGS

Various features and/or embodiments of this invention are illustrated in a drawing as described below. These features and/or embodiments are representative only, and the selection of these features and/or embodiments for inclusion in the drawing should not be interpreted as an indication that subject matter not included in the drawing is not suitable for practicing the invention, or that subject matter not included in the drawing is excluded from the scope of the appended claims and equivalents thereof.

DETAILED DESCRIPTION

Figure 1:
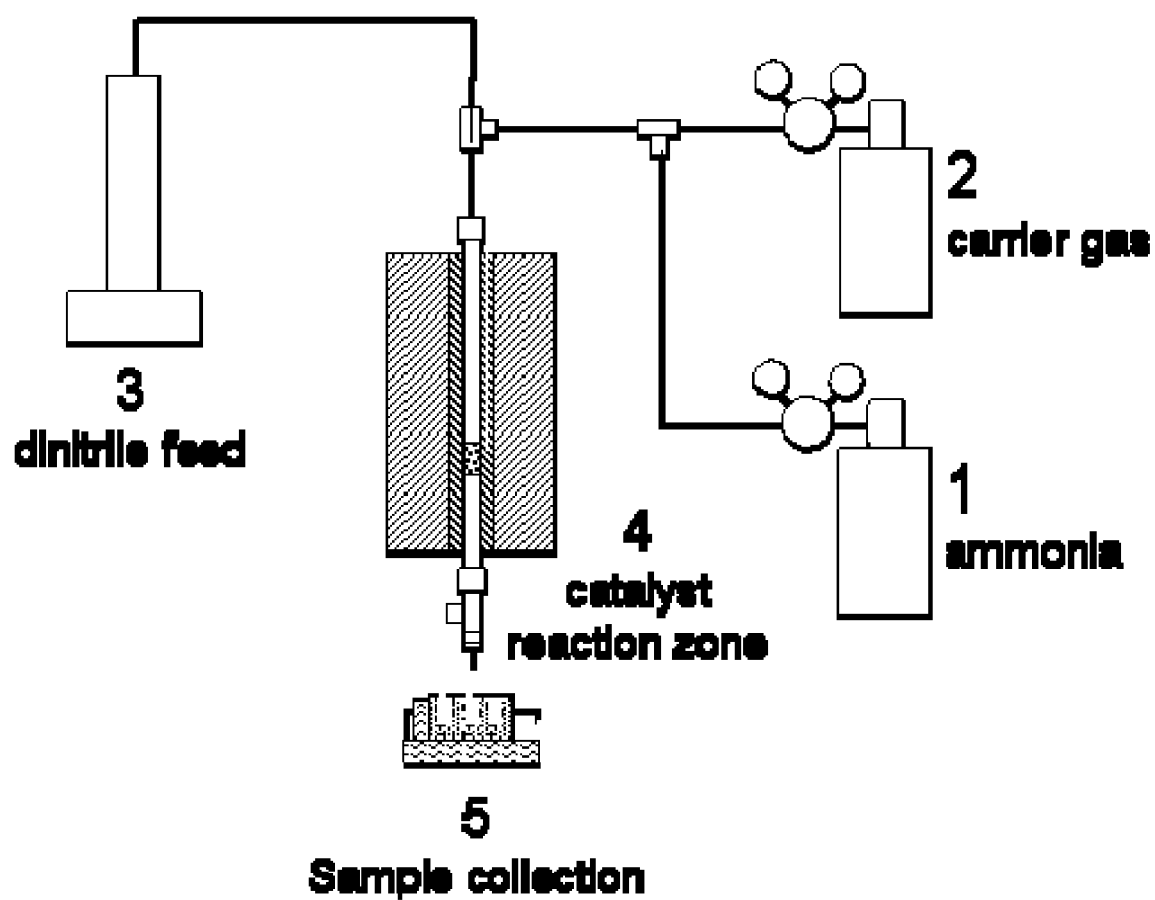
FIG. 1 is a schematic representation of a fixed-bed, gas-phase reactor as may be used in a process hereof.

In a process as described herein, there is provided a process for the gas-phase preparation of 2,6-diaminopyridine and related compounds from glutaronitrile and related compounds.

In one embodiment of the processes hereof, a diaminopyridine compound [as represented by the following structure of Formula (I)] may be synthesized from an acyclic dinitrile compound [as represented by the following structure of Formula (II)] by providing the acyclic dinitrile compound as a gas; providing ammonia gas, or a mixture of gaseous ammonia and a carrier gas; heating a dehydrogenation catalyst; and contacting the dinitrile compound and ammonia, or carrier gas mixture, in the presence of the heated catalyst to produce the desired diaminopyridine [Formula (I)] product.

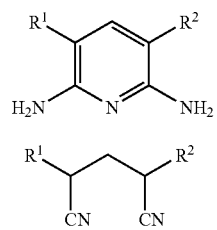

In Formulae (I) and (II), $R^1$ and $R^2$ are each independently selected from H, and a hydrocarbyl group. Examples of hydrocarbyl groups suitable for use in $R^1$ or $R^2$ include without limitation a $C_1$~$C_{12}$, $C_1$~$C_8$, $C_1$~$C_6$, or $C_1$~$C_4$, straight-chain or branched, saturated or unsaturated, substituted or unsubstituted, aliphatic hydrocarbyl group; and a $C_3$~$C_{12}$, $C_3$~$C_8$, or $C_3$~$C_6$, cyclic, saturated or unsaturated, substituted or unsubstituted, aliphatic hydrocarbyl group.

An unsubstituted hydrocarbyl group as described above contains no atoms other than carbon and hydrogen. In a substituted hydrocarbyl group, one or more heteroatoms selected from O, N, S and P may optionally be substituted for any one or more of the in-chain (i.e. non-terminal) or in-ring carbon atoms, provided that each heteroatom is separated from the next closest heteroatom by at least one and preferably two carbon atoms, and that no carbon atom is bonded to more than one heteroatom; and/or one or more halogen atoms may optionally be bonded to a terminal carbon atom.

In addition, however, a substituted $C_3$~$C_{12}$ cyclic hydrocarbyl group may contain one or more $C_1$~$C_8$, or $C_1$~$C_4$, straight-chain or branched, saturated or unsaturated, aliphatic hydrocarbyl groups bonded to a carbon atom in the ring structure, such group itself optionally being substituted with one or more heteroatoms selected from O, N, S and P, and/or containing one or more halogen atoms, subject to the conditions set forth above.

A $C_1$~$C_{12}$ straight-chain or branched, saturated or unsaturated, substituted or unsubstituted, aliphatic hydrocarbyl group suitable for use herein may include, for example, a methyl, ethyl, n-propyl, i-propyl, n-butyl, sec-butyl, tert-butyl, n-pentyl, n-hexyl, n-octyl, trimethylpentyl, allyl and/or propargyl group. An unsaturated aliphatic group may include one or more double bonds, such as in a dienyl or terpenyl structure, or a triple bond such as in an acetylenyl structure. A $C_3$~$C_{12}$ cyclic, saturated or unsaturated, substituted or unsubstituted, aliphatic hydrocarbyl group suitable for use herein may include, for example, an alicyclic functional group containing in its structure, as a skeleton, cyclohexane, cyclooctane, norbomane, norbornene, perhydro-anthracene, adamantane, or tricyclo-[5.2.1.0$^{2.6}$]-decane groups. Preferably, one or both of $R^1$ and $R^2$ are H.

When $R^1$ and $R^2$ are both H, the acyclic dinitrile is glutaronitrile ("GN") and the Formula (I) compound is 2,6-diaminopyridine ("DAP"), as represented by the structural formulae shown below:

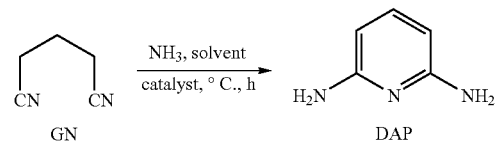

Various compounds of Formula (II), for use as a starting material herein, may be synthesized by processes known in the art, or are available commercially from suppliers such as Alfa Aesar (Ward Hill, Mass.), City Chemical (West Haven, Conn.), Fisher Scientific (Fairlawn, N.J.), Sigma-Aldrich (St. Louis, Mo.) or Stanford Materials (Aliso Viejo, Calif.).

In the processes hereof, a Formula (II) acyclic dinitrile compound is contacted with gaseous ammonia, or a mixture of gaseous ammonia and a carrier gas. The reaction is conducted in the gas phase, i.e. all components of the reaction mixture that react with each other have been exposed to sufficient heat to have been transformed to the gas phase, and the Formula (II) acyclic dinitrile compound and the ammonia is thus each provided to, and present in, the reaction mixture as a gas.

In a process hereof, a Formula (II) compound is contacted with ammonia in the presence of a heterogeneous dehydrogenation catalyst. A catalyst suitable for use in a process hereof is a substance that increases the rate of approach to equilibrium of the reaction without itself being substantially consumed in the reaction. A dehydrogenation catalyst suitable for use herein typically contains at least one metal, or metal salt, wherein the metal for use in the catalyst is selected, for example, from elements of Groups IVA, VA, VIA, VIIA, VIII, IB and/or IIB of the Periodic Table [as such groups are described, for example, in the periodic table in a reference such as *Advanced Inorganic Chemistry* by Cotton and Wilkinson, Interscience, New York, 2nd Ed. (1966)]. A particular metal, for use by itself or in a metal salt, may be selected from Group VIII elements such as iron, cobalt and nickel; and/or from the platinum group of metals including ruthenium, rhodium, palladium, osmium, iridium and platinum. The platinum group of metals and their salts are preferred, more preferably platinum and palladium and their salts. Sponge metal catalysts may also be used, including without limitation Raney iron, Raney nickel and Raney cobalt. Raney nickel is preferred.

In a heterogeneous catalyst, a metal or metal salt of the desired elements may be deposited on any support with a sufficiently high surface area. A heterogeneous catalyst may thus be distinguished from a homogeneous catalyst, which is not supported, in the sense that a homogeneous catalyst and the reactants reside in the same phase, which is uniform, and the catalyst is molecularly dispersed with the reactants in that phase.

The support for a heterogeneous catalyst as used herein may be amorphous or may possess a crystalline structure, or may contain both amorphous and crystalline portions. The support may be a solid metal oxide or solid non-metal oxide, each with surface —OH groups. Examples of such metal oxides are those from tri- and tetravalent metals, which may be a transition or non-transition metal or any rare earth such as alumina, titania, cobaltic oxide, zirconia, ceria, molybdenum oxide and tungsten oxide. An example of a typical non-metal oxide is silica. The support may also be a zeolite or zeotype material having a structure made up of tetrahedra joined together through oxygen atoms to produce an extended network with channels of molecular dimensions. The zeolite/zeotype materials typically have SiOH and/or AlOH groups on the external or internal surfaces. The support may also be activated carbon, coke or charcoal. Preferably, the support is at least one of alumina, silica, silicalite, ceria, titania, or carbon, more preferably alumina, silica or carbon.

The reaction is conducted by injecting a Formula (II) dinitrile compound and ammonia as reactants in gaseous form, together with a carrier gas if desired, into a reactor that is loaded with the desired catalyst. Providing a Formula (II) dinitrile compound to the reaction mixture in the gas phase may be accomplished by heating the Formula (II) dinitrile compound neat [i.e. the Formula (II) compound itself in the absence of solvent], or by heating a solution of the dinitrile compound in a volatilizable solvent such as ethanol, 1,4-dioxane, tetrahydrofuran or acetone. The compound or solution thereof is heated to a temperature such that it is vaporized before being injected into the reactor as a gas. Where, for example, the notation "solvent" is shown in the reaction scheme presented above for the case where glutaronitrile is reacted, it is to be understood that the entire solution—both the glutaronitrile and the solvent—are in vapor form at the time they are injected into the reactor. Mixed solvents can be used, but using the Formula (II) dinitrile compound in ethanol is preferred. Heating the Formula (II) dinitrile compound, or solution thereof, to a temperature in the range of about 250° C. to 300° C. is typically suitable to vaporize the compound or solution. Where it is used, the solvent is condensed along with the product after the reaction.

Ammonia, as anhydrous ammonia, has a boiling point of −33° C., and is therefore available as a gas at ambient temperatures, and may be used as such for injection into the reactor. Carrier gases suitable for use to dilute the concentration of ammonia in the reaction mixture may be used when desired, and these include nitrogen and other inert gases.

The reaction may occur in the gas phase at a temperature that may suitably be in the range of from about 200° C. to about 425° C., in the range of from above 300° C. to about 425° C., in the range of from about 310° C. to about 400° C., or in the range of from about 325° C. to about 400° C. The reaction temperature referred to here is the temperature that has been provided for the catalyst in the catalyst zone of the reactor. A temperature in these ranges is provided by heating the various portions of the reactor from a source external thereto, in particular a heating element designed to surround and heat the catalyst zone of the reactor, and thus the catalyst itself. The selected temperature thus exists in the catalyst zone of the reactor upon the occasion when the gaseous nitrile compound and ammonia gas are contacted in the presence of the catalyst.

The reaction may be run at ambient pressure, or at a pressure of up to about 2 atm or up to about 5 atm (up to about 0.2 or up to about 0.5 MPa), or at a pressure in the range of about 0.5 to about 3 atm (about 0.05 to about 0.3 MPa), or at a pressure in the range of about 0.5 to about 2 atm (about 0.05 to about 0.2 MPa), or at a pressure in the range of about 1 to about 1.5 atm (about 0.1 to about 0.15 MPa). The reaction may be run for a length of time of a minute or less, or for a length of time of about 5 to about 10 seconds, or of about 1 to about 2 seconds, or of less than one second. In all cases, however, the reaction is carried out at a temperature and pressure and for a time that is sufficient to obtain gas-phase production of a Formula (I) diaminopyridine reaction product.

In various embodiments, the amount of ammonia fed to the reactor may be in the range of from about 1 molar equivalent to about 700 molar equivalents, or in the range of from about 10 molar equivalents to 400 molar equivalents, or in the range of from about 25 molar equivalents to 300 molar equivalents, per molar equivalent of Formula (II) dinitrile compound that is fed in. In yet other embodiments, a diaminopyridine compound may be produced at a concentration in the range of from about 1 to about 400 molar equivalents per molar equivalent of the Formula (II) dinitrile compound used in the reaction.

Reactors suitable for use in the processes hereof include fixed-bed reactors, and pipe, tubular or other plug-flow reactors and the like in which the catalyst particles are held in place and do not move with respect to a fixed residence frame; or fluidized bed reactors. Reactants may be flowed into and through reactors such as these on a continuous basis to give a corresponding continuous flow of product at the downstream end of the reactor. These and other suitable reactors are more particularly described, for example, in Fogler, *Elements of Chemical Reaction Engineering*, 2nd Edition, Prentice-Hall Inc. (1992). One example of a continuous, fixed-bed, gas-phase reactor as used in an embodiment of the processes hereof is shown in FIG. 1. In a reactor such as shown in FIG. 1, in-flow lines are heat traced to keep reactants at a suitable temperature, and the temperature of the catalyst zone is controlled by a separate heating element at that location. The diaminopyridine product, as obtained from the reactor in the form of a gas, may be condensed by cooling to a liquid for ease of further handling.

A compound of Formula (I) (a "Pyridine Product"), after being produced for example in the manner as described above, may, as desired, be isolated and recovered. The Pyridine Product may also, however, be subjected with or without recovery from the reaction mixture to further steps to convert it to another product such as another compound (such as a type useful, for example, as a monomer), or an oligomer or a polymer. Another embodiment of a process hereof thus provides a process for converting a Pyridine Product, through a reaction (including a multi-step reaction), into another compound, or into an oligomer or a polymer. A Pyridine Product may be made by a process such as described above, and then converted, for example, by being subjected to a polymerization reaction to prepare an oligomer or polymer therefrom, such as those having amide functionality, imide functionality, or urea functionality, or a pyridobisimidazole-2,6-diyl(2,5-dihydroxy-p-phenylene) polymer.

A Pyridine Product such as a diaminopyridine may be converted into a polyamide oligomer or polymer by reaction with a diacid (or diacid halide) in a process in which, for example, the polymerization takes place in solution in an organic compound that is liquid under the conditions of the reaction, is a solvent for both the diacid(halide) and the diaminopyridine, and has a swelling or partial salvation action on the polymeric product. The reaction may be effected at moderate temperatures, e.g. under 100° C., and is preferably effected in the presence of an acid acceptor that is also soluble in the chosen solvent. Suitable solvents include methyl ethyl ketone, acetonitrile, N,N-dimethylacetamide dimethyl formamide containing 5% lithium chloride, and N-methyl pyrrolidone containing a quaternary ammonium chloride such as methyl tri-n-butyl ammonium chloride or methyl-tri-n-propyl ammonium chloride. Combination of the reactant components causes generation of considerable heat and the agitation, also, results in generation of heat energy. For that reason, the solvent system and other materials are cooled at all times during the process when cooling is necessary to maintain the desired temperature. Processes similar to the foregoing are described in U.S. Pat. No. 3,554,966; U.S. Pat. No. 4,737,571; and CA 2,355,316.

A Pyridine Product such as a diaminopyridine may also be converted into a polyamide oligomer or polymer by reaction with a diacid (or diacid halide) in a process in which, for example, a solution of the diaminopyridine in a solvent may be contacted in the presence of an acid acceptor with a solution of a diacid or diacid halide, such as a diacid chloride, in a second solvent that is immiscible with the first to effect polymerization at the interface of the two phases. The diaminopyridine may, for example, be dissolved or dispersed in a water containing base with the base being used in sufficient quantities to neutralize the acid generated during polymerization. Sodium hydroxide may be used as the acid acceptor. Preferred solvents for the diacid(halide) are tetrachloroethylene, methylenechloride, naphtha and chloroform. The solvent for the diacid(halide) should be a relative non-solvent for the amide reaction product, and be relatively immiscible in the amine solvent. A preferred threshold of immiscibility is as follows: an organic solvent should be soluble in the amine solvent not more than between 0.01 weight percent and 1.0 weight percent. The diaminopyridine, base and water are added together and vigorously stirred. High shearing action of the stirrer is important. The solution of acid chloride is added to the aqueous slurry. Contacting is generally carried out at from 0° C. to 60° C., for example, for from about 1 second to 10 minutes, and preferably from 5 seconds to 5 minutes at room temperature. Polymerization occurs rapidly. Processes similar to the foregoing are described in U.S. Pat. No. 3,554,966 and U.S. Pat. No. 5,693,227.

A Pyridine Product such as a diaminopyridine may also be converted into a polyimide oligomer or polymer by reaction with a tetraacid (or halide derivative thereof) or a dianhydride in a process in which each reagent (typically in equimolar amounts) is dissolved in a common solvent, and the mixture is heated to a temperature in the range of 100~250° C. until the product has a viscosity in the range of 0.1~2 dL/g. Suitable acids or anhydrides include benzhydrol 3,3',4,4'-tetracarboxylic acid, 1,4-bis(2,3-dicarboxyphenoxy)benzene dianhydride, and 3,3',4,4'-benzophenone tetracarboxylic acid dianhydride. Suitable solvents include cresol, xylenol, diethyleneglycol diether, gamma-butyrolactone and tetramethylenesulfone. Alternatively, a polyamide-acid product may be recovered from the reaction mixture and advanced to a polyimide by heating with a dehydrating agent such as a mixture of acetic anhydride and beta picoline. Processes similar to the foregoing are described in U.S. Pat. No. 4,153,783; U.S. Pat. No. 4,736,015; and U.S. Pat. No. 5,061,784.

A Pyridine Product such as a diaminopyridine may also be converted into a polyurea oligomer or polymer by reaction with a polyisocyanate, representative examples of which include toluene diisocyanate; methylene bis(phenyl isocyanates); hexamethylene diisocycanates; phenylene diisocyanates. The reaction may be run in solution, such as by dissolving both reagents in a mixture of tetramethylene sulfone and chloroform with vigorous stirring at ambient temperature. The product can be worked up by separation with water, or acetone and water, and then dried in a vacuum oven. Processes similar to the foregoing are described in U.S. Pat. No. 4,451,642 and Kumar, Macromolecules 17, 2463 (1984). The polyurea forming reaction may also be run under interfacial conditions, such as by dissolving the diaminopyridine in an aqueous liquid, usually with an acid acceptor or a buffer. The polyisocyanate is dissolved in an organic liquid such as benzene, toluene or cyclohexane. The polymer product forms at the interface of the two phases upon vigourous stirring. Processes similar to the foregoing are described in U.S. Pat. No. 4,110,412 and Millich and Carraher, Interfacial Syntheses, Vol. 2, Dekker, New York, 1977. A diaminopyridine may also be converted into a polyurea by reaction with phosgene, such as in an interfacial process as described in U.S. Pat. No. 2,816,879.

A Pyridine Product such as a tetraamino pyridine may be converted to a pyridobisimidazole-2,6-diyl(2,5-dihydroxy-p-phenylene) polymer by polymerizing a 2,5-dihydroxyterephthalic acid with the trihydrochloride-monohydrate of tetraaminopyridine in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by mixing the monomers at a temperature from about 50° C. to about 110° C., and then 145° C. to form an oligomer, and then reacting the oligomer at a temperature of about 160° C. to about 250° C. as disclosed in U.S. Patent Publication 2006/0287475 (which is incorporated in its entirety as a part hereof for all purposes). The pyridobisimidazole-2,6-diyl(2,5-dihydroxy-p-phenylene) polymer so produced may be, for example, a poly(1,4-(2,5-dihydroxy)phenylene-2,6-pyrido[2,3-d:5,6-d']bisimidazole) polymer, or a poly[(1,4-dihydrodiimidazo[4,5-b:4',5'-e]pyridine-2,6-diyl)(2,5-dihydroxy-1,4-phenylene)] polymer. The pyridobisimidazole portion thereof may, however, be replaced by any or more of a benzobisimidazole, benzobisthiazole, benzobisoxazole, pyridobisthiazole and a pyridobisoxazole; and the 2,5-dihydroxy-p-phenylene portion thereof may be replaced by the derivative of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole.

EXAMPLES

The advantageous attributes and effects of the processes hereof may be seen in a series of examples (Examples 1~62), as described below. The embodiments of these processes on which the examples are based are representative only, and the selection of those embodiments to illustrate the invention does not indicate that conditions, arrangements, approaches, regimes, steps, techniques, configurations, protocols or reactants not described in these examples are not suitable for practicing these processes, or that subject matter not described in these examples is excluded from the scope of the appended claims and equivalents thereof.

Materials.

The following materials were used in the examples. Commercial reagents, such as glutaronitrile (99%), ethanol (99.5%), and 2,6-diaminopyridine (98%), were obtained from Aldrich Chemical Company (Milwaukee, Wis., USA), and used as received unless otherwise noted. Palladium (0.5 weight percent on alumina as 1/16-inch round beads), platinum (0.5 weight percent on activated alumina, and 1.0 percent on alumina/silica) catalysts were obtained from Engelhard Corporation (now BASF Catalysts LLC, Florham Park, N.J., USA), and used as received unless otherwise noted. Anhydrous ammonia (99.99%) and nitrogen were obtained from MG Industries (Malvern, Pa., USA), and used as received unless otherwise specified.

Methods

In these examples, the following protocol was used (except as noted in the description of a particular example): the reactions were carried out in a custom fixed-bed gas phase reactor fabricated from 3/8-inch (0.95-cm) 316 S.S. tubing (numerical references below being to FIG. 1). The reactor was operated under continuous flow of gaseous mixtures of anhydrous ammonia (1), a carrier-gas such as nitrogen (2), and organic reactants. The organic reactants were optionally dissolved in a solvent, such as ethanol, and were metered as a liquid by a syringe pump (Isco Model 100 DM) (3) and flashed to the vapor state by passing the liquid feed through a heated injector into the combined and heated ammonia and carrier gas. The ammonia and carrier gases were metered with mass flow controllers (Brooks Model 5850E). The inlet lines and liquid injector were heat traced with electrical heating tape to flash the liquid organic feed stream to vapor and to pre-heat the reactor feeds prior to contacting the catalyst reaction zone (4). The reactor and catalyst reaction zone was heated with an electrical tube furnace. The reactor effluent was passed through a condenser and then a syringe needle into vented and chilled sample vials where the liquid products were condensed and collected, and the carrier gas and unreacted ammonia were vented to a fume hood containing the entire apparatus. A circulating bath was used to chill these sample recovery vials (5).

The meaning of abbreviations as used in the examples is as follows: "DAP" means 2,6-diaminopyridine, "GN" means glutaronitrile, "eq" means equivalent, "h" means hour(s), "g" means gram(s), "mg" means milligrams, "min" means minute(s), "mL" means milliliter(s), "mol" means mole, "mmol" means millimole(s), "µmol" means micromole(s), "Pd/Al$_2$O$_3$" means palladium on alumina catalyst, "Pt/Al$_2$O$_3$" means platinum on alumina catalyst, "Pt/Al$_2$O$_3$.SiO$_2$" means platinum on alumina/silica catalyst, "scc" means standard cubic centimeter (cubic centimeters at standard conditions of temperature and pressure), "GC" means gas chromatography, "NMR" means nuclear magnetic resonance spectroscopy, "TLC" means thin-layer chromatography, and "LDL" means lower-detection limit.

In Examples 1~62, qualitative and quantitative evidence for DAP formation is determined by TLC (silica gel 60 F$_{254}$ plates (2.5×7.5 cm)), $^1$H NMR, and/or GC (HP5890 Series II equipped with FID detector) with comparison of crude product mixtures with authentic material as specified. For TLC, the LDL was confirmed to be less than 1 µmol/mL. The temperature reported is the temperature at the catalyst zone of the reactor.

Examples 1-4

The reactor zone was charged with 2 g catalyst and preheated to approximately 300° C. The reactor inlet lines were pre-heated to approximately 250° C. Once the temperatures had equilibrated, gas flows were set at 100 scc ammonia per min and 1000 scc nitrogen per minute, respectively. A solution of glutaronitrile (2.49 g, 26.43 mmol) in ethanol (37.71 g, 818.5 mmol) was loaded into the syringe pump and fed to the reaction zone at flow rates per those indicated in Table 1. Following reaction at the specified conditions, DAP was detected by TLC and GC analysis methods for all examples. Additionally, DAP was also confirmed in Example 4 by $^1$H NMR analysis.

TABLE 1

Examples 1-4
Fixed-bed gas-phase conversion of GN to DAP.

|  | catalyst | Temp. (° C.) | GN flow rate (gmol/min) | NH3:GN (molar ratio) | relative % DAP/recovered GN |
|---|---|---|---|---|---|
| Example 1 | 0.5% Pd/Al2O3 | 309 | 1.23E−04 | 36 | 1.3 |
| Example 2 | 0.5% Pd/Al2O3 | 309 | 8.07E−05 | 55 | 1.0 |
| Example 3 | 0.5% Pd/Al2O3 | 308 | 1.70E−05 | 263 | 2.6 |
| Example 4 | 0.5% Pd/Al2O3 | 309 | 6.37E−06 | 701 | 5.3 |

Examples 5-14

The reactor zone was charged with 2 g catalyst and preheated to approximately 300° C. Reactor inlet lines were pre-heated to approximately 250° C. Once the temperatures had equilibrated, gas flows were set at 10 scc ammonia per min and 1000 scc nitrogen per minute, respectively. A solution of glutaronitrile (45.0 g, 478.11 mmol) in ethanol (5.0 g, 108.53 mmol) was loaded into the syringe pump and fed to the reaction zone at flow rates and reactor temperatures per those indicated in Table 2. Following reaction at the specified condition, DAP was detected by TLC analysis in each example.

TABLE 2

Examples 5-14.
Qualitative fixed-bed gas-phase conversion of GN to DAP.

|  | catalyst | Temp. (° C.) | GN flow rate (gmol/min) | NH3:GN (molar ratio) |
|---|---|---|---|---|
| Example 5 | 0.5% Pd/Al2O3 | 296 | 1.12E−04 | 4 |
| Example 6 | 0.5% Pd/Al2O3 | 290 | 2.24E−04 | 2 |
| Example 7 | 0.5% Pd/Al2O3 | 302 | 4.47E−04 | 1 |

TABLE 2-continued

Examples 5-14.
Qualitative fixed-bed gas-phase conversion of GN to DAP.

| catalyst | Temp. (° C.) | GN flow rate (gmol/min) | NH3:GN (molar ratio) |
| --- | --- | --- | --- |
| Example 8 | 0.5% Pd/Al2O3 | 302 | 8.95E−04 | 0.5 |
| Example 9 | 0.5% Pd/Al2O3 | 353 | 1.12E−04 | 4 |
| Example 10 | 0.5% Pd/Al2O3 | 360 | 2.24E−04 | 2 |
| Example 11 | 0.5% Pd/Al2O3 | 405 | 1.12E−04 | 4 |
| Example 12 | 0.5% Pd/Al2O3 | 406 | 2.24E−04 | 2 |
| Example 13 | 0.5% Pd/Al2O3 | 405 | 4.47E−04 | 1 |
| Example 14 | 0.5% Pd/Al2O3 | 398 | 8.95E−04 | 0.5 |

Examples 15-26

The reactor zone was charged with 2 g catalyst and pre-heated to approximately 300° C. Reactor inlet lines were pre-heated to approximately 250° C. Once the temperatures had equilibrated, gas flows were set at 10 scc ammonia per min and 1000 scc nitrogen per minute, respectively. A solution of glutaronitrile (45.0 g, 478.11 mmol) in ethanol (5.0 g, 108.53 mmol) was loaded into syringe pump and fed to the reaction zone at flow rates and reactor temperatures per those indicated in Table 3. Following reaction at the specified condition, DAP was detected by TLC analysis in each Example.

TABLE 3

Examples 15-26.:
Qualitative fixed-bed gas-phase conversion of GN to DAP,

| catalyst | Temp. (° C.) | GN flow rate (gmol/min) | NH3:GN (molar ratio) |
| --- | --- | --- | --- |
| Example 15 | 1% Pt/Al2O3•SiO2 | 296 | 1.12E−04 | 4 |
| Example 16 | 1% Pt/Al2O3•SiO2 | 304 | 2.24E−04 | 2 |
| Example 17 | 1% Pt/Al2O3•SiO2 | 304 | 4.47E−04 | 1 |
| Example 18 | 1% Pt/Al2O3•SiO2 | 302 | 8.95E−04 | 0.5 |
| Example 19 | 1% Pt/Al2O3•SiO2 | 349 | 1.12E−04 | 4 |
| Example 20 | 1% Pt/Al2O3•SiO2 | 349 | 2.24E−04 | 2 |
| Example 21 | 1% Pt/Al2O3•SiO2 | 350 | 4.47E−04 | 1 |
| Example 22 | 1% Pt/Al2O3•SiO2 | 355 | 8.95E−04 | 0.5 |
| Example 23 | 1% Pt/Al2O3•SiO2 | 400 | 1.12E−04 | 4 |
| Example 24 | 1% Pt/Al2O3•SiO2 | 398 | 2.24E−04 | 2 |
| Example 25 | 1% Pt/Al2O3•SiO2 | 398 | 4.47E−04 | 1 |
| Example 26 | 1% Pt/Al2O3•SiO2 | 406 | 8.95E−04 | 0.5 |

Examples 27-30

The reactor zone was charged with 4 g catalyst and pre-heated to approximately 300° C. Reactor inlet lines were pre-heated to approximately 300° C. Once the temperatures had equilibrated, gas flow was set at 600 scc ammonia per min. A solution of glutaronitrile (12.5 g, 132.81 mmol) in ethanol (37.57 g, 813.98 mmol) was loaded into syringe pump and fed to the reaction zone at flow rates and reactor temperatures per those indicated in Table 4. Following reaction at the specified condition, DAP was detected by TLC analysis in each example.

TABLE 4

Examples 27-30.:
Qualitative fixed-bed gas-phase conversion of GN to DAP,

| catalyst | Temp. (° C.) | GN flow rate (gmol/min) | NH3:GN (molar ratio) |
| --- | --- | --- | --- |
| Example 27 | 1% Pt/Al2O3•SiO2 | 297 | 1.12E−04 | 240 |
| Example 28 | 1% Pt/Al2O3•SiO2 | 297 | 4.47E−04 | 60 |
| Example 29 | 1% Pt/Al2O3•SiO2 | 348 | 1.12E−04 | 240 |
| Example 30 | 1% Pt/Al2O3•SiO2 | 403 | 1.12E−04 | 240 |

Examples 31-34

The reactor zone was charged with 2 g catalyst and pre-heated to approximately 160° C. Reactor inlet lines were pre-heated to approximately 160° C. Once the temperatures had equilibrated, gas flow was set at 1000 scc ammonia per min. A solution of glutaronitrile (25.0 g, 265.62 mmol) in ethanol (75.0 g, 1.63 mol) was loaded into the syringe pump and fed to the reaction zone at flow rates and reactor temperatures per those indicated in Table 5. Following reaction at the specified condition, DAP was detected by TLC analysis in each example.

TABLE 5

Examples 31-34.:
Qualitative fixed-bed gas-phase conversion of GN to DAP,

| catalyst | Temp. (° C.) | GN flow rate (gmol/min) | NH3:GN (molar ratio) |
| --- | --- | --- | --- |
| Example 31 | 0.5% Pd/Al2O3 | 305 | 1.12E−04 | 400 |
| Example 32 | 0.5% Pd/Al2O3 | 305 | 4.47E−04 | 100 |
| Example 33 | 0.5% Pd/Al2O3 | 348 | 1.12E−04 | 400 |
| Example 34 | 0.5% Pd/Al2O3 | 348 | 4.47E−04 | 100 |

Examples 35-42

The reactor zone was charged with 2 g catalyst and pre-heated to approximately 300° C. Reactor inlet lines were pre-heated to approximately 325° C. Once the temperatures had equilibrated, gas flows were modified according to the conditions specified in Table 6. A solution of glutaronitrile (25.0 g, 265.62 mmol) in ethanol (75.0 g, 1.63 mol) was loaded into syringe pump and fed to the reaction zone at flow rates and reactor temperatures per those indicated in Table 6. Following reaction at the specified condition, DAP was detected by TLC analysis in each example.

TABLE 6

Examples 35-42.:
Qualitative fixed-bed gas-phase conversion of GN to DAP.

|  | catalyst | Temp. (° C.) | GN flow rate (gmol/min) | NH3 flow rate (scc/min) | N2 flow rate (scc/min) | NH3:GN (molar ratio) |
|---|---|---|---|---|---|---|
| Example 35 | 0.5% Pd/Al2O3 | 309 | 1.12E−04 | 1000 | 0 | 400 |
| Example 36 | 0.5% Pd/Al2O3 | 299 | 4.47E−04 | 1000 | 0 | 100 |
| Example 37 | 0.5% Pd/Al2O3 | 299 | 1.12E−04 | 600 | 400 | 240 |
| Example 38 | 0.5% Pd/Al2O3 | 306 | 4.47E−04 | 600 | 400 | 60 |
| Example 39 | 0.5% Pd/Al2O3 | 303 | 1.12E−04 | 600 | 0 | 240 |
| Example 40 | 0.5% Pd/Al2O3 | 300 | 4.47E−04 | 600 | 0 | 60 |
| Example 41 | 0.5% Pd/Al2O3 | 300 | 1.12E−04 | 360 | 240 | 144 |
| Example 42 | 0.5% Pd/Al2O3 | 301 | 4.47E−04 | 360 | 240 | 36 |

Examples 43-62

To demonstrate the feasibility of running a reaction as described herein continuously, the reactor zone was charged with 2 g catalyst and pre-heated to approximately 300° C. Reactor inlet lines were pre-heated to approximately 300° C. Once the temperatures had equilibrated, gas flows were set at 600 scc ammonia per min. A solution of glutaronitrile (25.0 g, 265.62 mmol) in ethanol (75.0 g, 1.63 mol) was loaded into syringe pump and fed to the reaction zone at constant liquid flow rate of 0.05 mL/min (1.12×10$^{-04}$ gmol/min glutaronitrile) with reactor temperature approximately 300° C. Following reaction at the specified condition, samples were taken approximately in 10 minute intervals for approximately 200 minutes as indicated in Table 7. DAP was detected by TLC analysis in each sample.

TABLE 7

Examples 43-62.:
Qualitative continuous fixed-bed
gas-phase conversion of GN to DAP

|  | catalyst | Temp. (° C.) | Time (min.) | GN flow rate (gmol/min) | NH3:GN (molar ratio) |
|---|---|---|---|---|---|
| Example 43 | 0.5% Pd/Al2O3 | 305 | 10 | 1.12E−04 | 240 |
| Example 44 | 0.5% Pd/Al2O3 | 298 | 20 | 1.12E−04 | 240 |
| Example 45 | 0.5% Pd/Al2O3 | 300 | 30 | 1.12E−04 | 240 |
| Example 46 | 0.5% Pd/Al2O3 | 300 | 40 | 1.12E−04 | 240 |
| Example 47 | 0.5% Pd/Al2O3 | 299 | 50 | 1.12E−04 | 240 |
| Example 48 | 0.5% Pd/Al2O3 | 300 | 60 | 1.12E−04 | 240 |
| Example 49 | 0.5% Pd/Al2O3 | 300 | 70 | 1.12E−04 | 240 |
| Example 50 | 0.5% Pd/Al2O3 | 300 | 80 | 1.12E−04 | 240 |
| Example 51 | 0.5% Pd/Al2O3 | 300 | 90 | 1.12E−04 | 240 |
| Example 52 | 0.5% Pd/Al2O3 | 300 | 100 | 1.12E−04 | 240 |
| Example 53 | 0.5% Pd/Al2O3 | 300 | 110 | 1.12E−04 | 240 |
| Example 54 | 0.5% Pd/Al2O3 | 300 | 120 | 1.12E−04 | 240 |
| Example 55 | 0.5% Pd/Al2O3 | 301 | 130 | 1.12E−04 | 240 |
| Example 56 | 0.5% Pd/Al2O3 | 300 | 140 | 1.12E−04 | 240 |
| Example 57 | 0.5% Pd/Al2O3 | 300 | 150 | 1.12E−04 | 240 |
| Example 58 | 0.5% Pd/Al2O3 | 300 | 160 | 1.12E−04 | 240 |
| Example 59 | 0.5% Pd/Al2O3 | 300 | 170 | 1.12E−04 | 240 |
| Example 60 | 0.5% Pd/Al2O3 | 300 | 180 | 1.12E−04 | 240 |
| Example 61 | 0.5% Pd/Al2O3 | 300 | 190 | 1.12E−04 | 240 |
| Example 62 | 0.5% Pd/Al2O3 | 300 | 200 | 1.12E−04 | 240 |

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage,
(a) amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value;
(b) all numerical quantities of parts, percentage or ratio are given as parts, percentage or ratio by weight;
(c) use of the indefinite article "a" or "an" with respect to a statement or description of the presence of an element or feature of this invention, does not limit the presence of the element or feature to one in number; and
(d) the words "include", "includes" and "including" are to be read and interpreted as if they were followed by the phrase "without limitation" if in fact that is not the case.

What is claimed is:

1. A process for the synthesis of a compound as represented by the following structure of Formula (I)

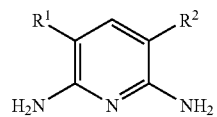

I comprising (a) providing a compound as represented by the following structure of Formula (II)

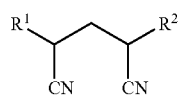

II in the form of a gas, (b) providing ammonia gas, or a mixture of ammonia gas and a carrier gas, (c) heating a heterogeneous dehydrogenation catalyst, and (d) contacting the Formula II compound and the ammonia, or mixture with carrier gas, in the presence of the catalyst to produce a Formula (I) product; wherein $R^1$ and $R^2$ are each independently selected from H and a hydrocarbyl group.

2. A process according to claim 1 wherein a hydrocarbyl group is selected from
a $C_1$~$C_{12}$ straight-chain or branched, saturated or unsaturated, substituted or unsubstituted, aliphatic hydrocarbyl group; and
a $C_3$~$C_{12}$ cyclic, saturated or unsaturated, substituted or unsubstituted, aliphatic hydrocarbyl group.

3. A process according to claim 1 wherein one or both of $R^1$ and $R^2$ are selected from a $C_1$~$C_4$ straight-chain or branched, saturated or unsaturated, substituted or unsubstituted, aliphatic hydrocarbyl group; and H.

4. A process according to claim 1 wherein $R^1$ and $R^2$ are both H.

5. A process according to claim 1 wherein the catalyst is heated to a temperature in the range of from about 200° C. to about 425° C.

6. A process according to claim 1 wherein the catalyst is heated to a temperature in the range of from above 300° C. to about 425° C.

7. A process according to claim 1 which is run at a pressure of up to about 0.5 MPa.

8. A process according to claim 1 wherein the heterogeneous dehydrogenation catalyst comprises at least one metal or metal salt and a support, wherein the metal, or the metal of a salt, is selected from elements of Groups IVA, VA, VIA, VIIA, VIII, IB and/or IIB of the Periodic Table.

9. A process according to claim 8 wherein the metal, or the metal of a salt, is selected from one or more members of the group consisting of iron, cobalt, nickel, ruthenium, rhodium, palladium, osmium, iridium, platinum, Raney iron, Raney nickel, Raney cobalt, copper and rhenium.

10. A process according to claim 8 wherein the metal, or the metal of a salt, is selected from one or more members of the group consisting of palladium and platinum; and the support comprises one or more materials selected from the group consisting of alumina, silica and activated carbon.

11. A process according to claim 8 wherein the support comprises one or more materials selected from the group consisting of alumina, titania, cobaltic oxide, zirconia, ceria, molybdenum oxide, tungsten oxide, silica, silicalite, a zeolite or zeotype material, activated carbon, coke and charcoal.

12. A process according to claim 8 wherein the support comprises one or more materials selected from the group consisting of alumina, silica, silicalite, ceria, titania and carbon.

13. A process according to claim 8 wherein $R^1$ and $R^2$ are both H; and the heterogeneous dehydrogenation catalyst comprises palladium or platinum, and/or a support comprising one or more materials selected from the group consisting of alumina, silica and activated carbon.

14. A process according to claim 1 wherein the Formula (II) compound is dissolved in a solvent to form a solution, and the solution is vaporized.

15. A process according to claim 1 wherein ammonia is admixed with a nitrogen carrier gas.

16. A process according to claim 1 which is run for a time of less than one minute.

17. A process according to claim 1 wherein the amount of ammonia fed to the reactor is in the range of from about 1 molar equivalent to about 700 molar equivalents per molar equivalent of Formula (II) dinitrile compound that is fed in.

18. A process according to claim 1 which is continuous.

19. A process according to claim 1 further comprising a step of subjecting the Formula (I) compound to a reaction to prepare therefrom a compound, oligomer or polymer.

20. A process according to claim 19 wherein a polymer prepared comprises a pyridobisimidazole-2,6-diyl(2,5-dihydroxy-p-phenylene) polymer, or a poly[(1',4-dihydrodiimidazo[4,5-b:4',5'-e]pyridine-2,6-diyl) (2,5-dihydroxy-1,4-phenylene)] polymer.

* * * * *